United States Patent [19]

Carangelo et al.

[11] Patent Number: 5,440,143
[45] Date of Patent: Aug. 8, 1995

[54] FOLDED-PATH OPTICAL ANALYSIS GAS CELL

[75] Inventors: Robert M. Carangelo, Glastonbury, Conn.; David D. Wright, Vershire, Vt.

[73] Assignee: On-Line Technologies, Inc., East Hartford, Conn.

[21] Appl. No.: 201,814

[22] Filed: Feb. 25, 1994

[51] Int. Cl.⁶ .......................................... G01N 15/06
[52] U.S. Cl. ..................................... 250/573; 356/246
[58] Field of Search ............... 250/343, 345, 573, 574, 250/575, 353; 356/432, 346, 246

[56] References Cited

U.S. PATENT DOCUMENTS 4,657,397 4/1987 Oehler et al. ...................... 356/414
4,749,276 6/1988 Bragg et al. ........................ 356/246

OTHER PUBLICATIONS

"Long Optical Paths of Large Aperture" by John U. White—J. Opt Soc. Am., No. 32 (1942) pp. 285–288.

*Primary Examiner*—David C. Nelms
*Attorney, Agent, or Firm*—Ira S. Dorman

[57] ABSTRACT

A folded-path gas cell employs an elliptical concave mirror in confronting relationship to two substantially spherical concave mirrors. At least one of the spherical mirrors, and usually both, are formed with an added cylindrical component to increase orthogonal focii coincidence and thereby to increase the radiation energy throughput characteristic of the cell.

11 Claims, 5 Drawing Sheets

FOLDED-PATH OPTICAL ANALYSIS GAS CELL

The United States Government has rights in this invention pursant to Contract No. DE-FG05-92ER81339, awarded by the Department of Energy.

BACKGROUND OF THE INVENTION

Folded-path cells for measuring optical absorption of gas-phase samples are well known in the art. Path lengthening, for increased analytical accuracy, is achieved therein through multiple reflection and traversal of the cell chamber by the analysis radiation beam.

In the so-called "White cell," which represents the seminal development in the field, the desired effect is produced by use of two side-by-side spherical objective mirrors arranged in confronting relationship to a third such mirror functioning as the field reflector (John U. White, "Long Optical Paths of Large Aperture", J. Opt. Soc. Am, No. 32 (1942), pp 285-288). A thermally stabilized long-path absorption cell of similar kind is described in Bragg et al, U.S. Pat. No. 4,749,276.

The demand remains however for a folded-path gas cell that enables further increases in effective path length, with more radiation throughput and less image blur. Such improvements would minimize energy losses and thereby serve to best preserve the resolution capability of associated optical instruments, as is essential for optimization of gas-phase quantitation.

SUMMARY OF THE INVENTION

Accordingly, it is the broad object of the present invention to provide a folded-path gas cell that is capable of higher radiation throughput and less image blur, as compared to prior art cells of equal or greater size, to thereby afford better operating parameters and to optimize the performance of associated optical instruments, by preservation of resolution capability.

More specific objects of the invention are to provide a gas cell having the foregoing features and advantages which, in addition, is of relatively incomplex design, exhibits minimal distortion and high optical stability under varying thermal conditions, and is of relatively facile and economic manufacture.

A related object of the invention is to provide an improved optical instrument incorporating a folded-path gas-analysis cell.

It has now been found that certain of the foregoing and related objects are attained by the provision of a radiation absorption gas cell comprised of an enclosure defining a substantially closed chamber, the cell having means for the introduction and withdrawal of gas and having spaced input and output windows formed through one end and aligned on a first axis. A concave reflective field surface extends at least partially between the windows, and a pair of substantially spherical, concave reflective objective surfaces are disposed in confronting relationship to the field surface at the opposite end of the enclosure. The objective surfaces are aligned side-by-side on an axis parallel to the first axis, in optical registry with the windows and with their centers of curvature located behind the field surface. At least one of the objective reflective surfaces has a superimposed cylindrical component, which serves to increase coincidence of focii in two orthogonal planes taken through the cell chamber, and thereby to maximize the energy throughput characteristic of the cell.

In preferred embodiments, the superimposed cylindrical component will extend parallel to the aforesaid axes, and both of the objective reflective surfaces will be so modified; the reflective field surface will most desirably be elliptical, with its major axis also lying parallel to those axes. The entire cell enclosure will advantageously be made in relatively thick sections of the same, high thermal conductivity material to ensure that dimensional changes occur uniformly throughout, and the reflective surfaces will desirably be machined directly upon the end pieces of which the enclosure is comprised.

Other objects of the invention are attained by the provision of a spectrometer in combination with the folded-path gas cell herein described. Such an instrument will include radiation source means, means for discriminating radiation as a function of wavelength (e.g., an interferometer, a dispersing element, a filter wheel), a detector responsive to radiation from the source, suitable transfer optics, electronic data-processing means, etc.; it will most desirably comprise a Fourier-transform infrared spectrometer.

DETAILED DESCRIPTION OF THE PREFERRED AND ILLUSTRATED EMBODIMENTS

Figure 1:
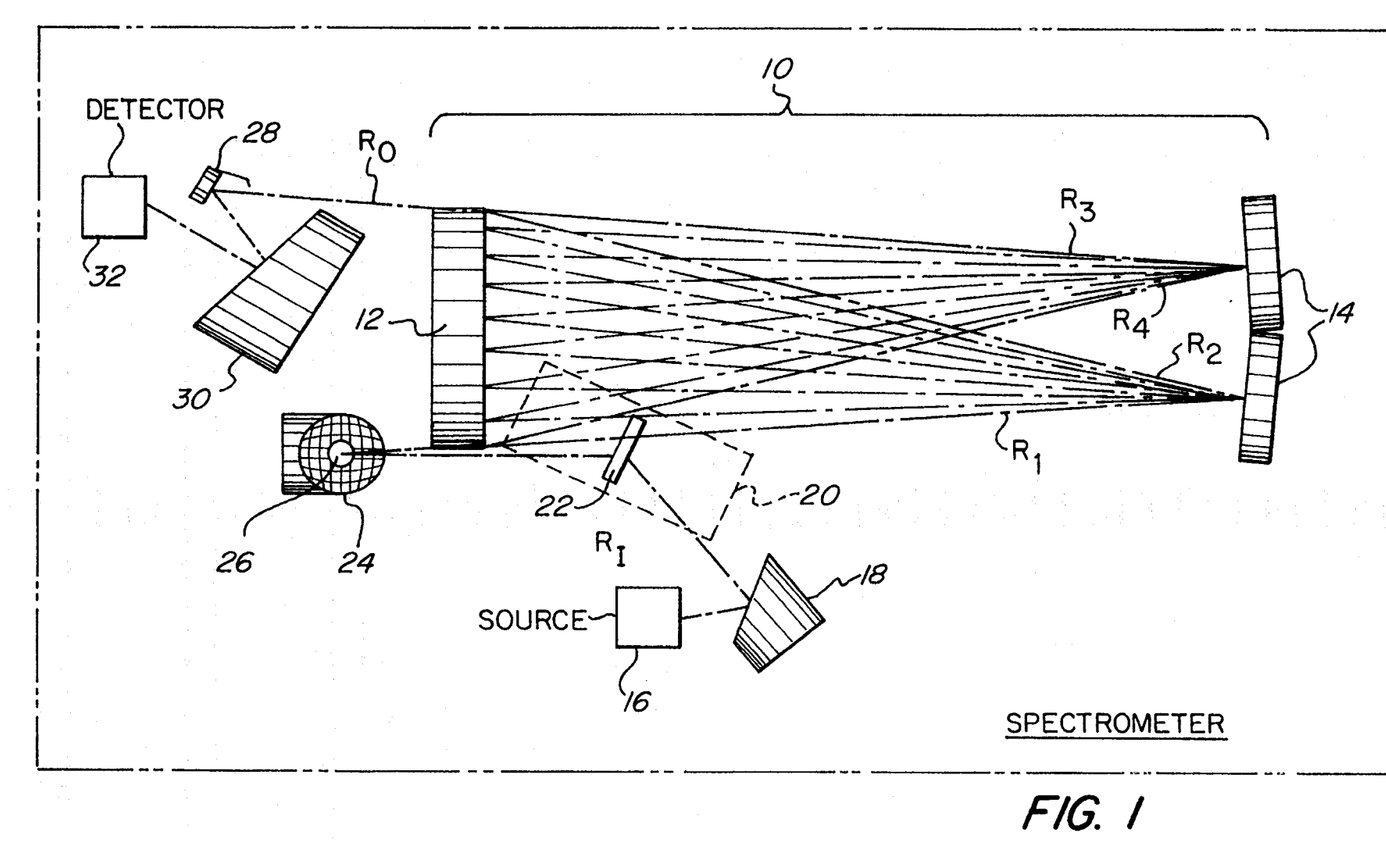
FIG. 1 is a diagrammatic illustration of a spectrometer in which is incorporated the novel folded-path gas cell of the present invention.

Turning initially to FIG. 1 of the drawings, therein illustrated diagrammatically is a spectrometer in which is incorporated a folded-path gas cell 10 embodying the present invention, the cell being comprised of a field reflector 12 and two objective reflectors 14. Input radiation $R_I$ originates at the source 16 and is reflected by a parabolic mirror 18 into the interferometer 20, as represented by the beamsplitter 22 thereof. The modulated beam exiting the interferometer 20 impinges upon a parabolic mirror 24 and is projected upwardly thereby onto a flat mirror 26, by which it is projected into the gas cell 10.

In traversing the cell cavity, the principal input radiation ray $R_I$ initially follows the path $R_1$, $R_2R_3$, and $R_4$, between object mirrors 14 and the field mirror 12. After making multiple passes, the radiation exits the cell as output beam $R_O$, which is reflected by a hyperbolic mirror 28 and an elliptical mirror 30 onto a photoconductive detector 32. As is the nature of such folded-path gas cells, the input radiation $R_I$ produces images at multiple points along the length of the field mirror 12, and at two or more levels to prevent their mutual interference, supplemental reflective elements (not shown) being provided within the cell as may be desired to multiply the number of image rows produced.

Figure 2:
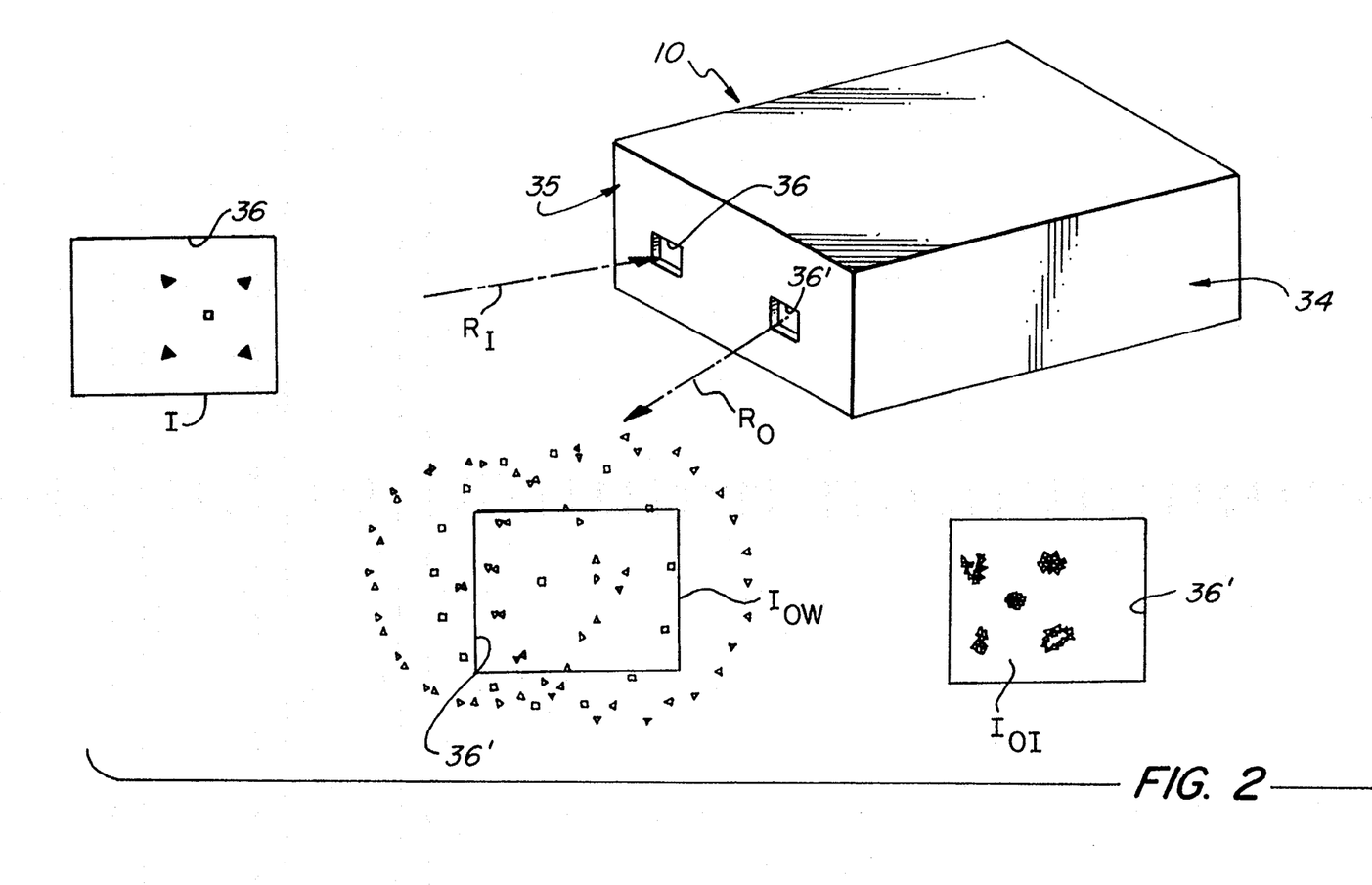
FIG. 2 is a diagrammatic representation of a gas cell, and of comparative, computer-generated images relevant thereto.

As depicted in FIG. 2, the enclosure of the cell 10 is seen to include a body, generally designated by the numeral 34, and an end piece generally designated by the numeral 35 (the opposite end piece 38 not being visible in this Figure). Apertures 36, 36′ are formed through the end piece 35 for the entry and exit of input radiation $R_I$ and output radiation $R_O$, respectively.

Boxes I, $I_{OI}$ and $I_{OW}$ of FIG. 2 indicate, respectively, an input image (comprised of rays from five points), the corresponding output image produced from a cell embodying the invention, and a comparable output image produced from a White cell (constructed as hereinabove described), as produced by radiation passing through the windows 36 and 36′. It is noted that the output image at box $I_{OW}$ is far more scattered and indistinct than is that at box $I_{OI}$, which is only slightly blurred; moreover, the image at box $I_{OW}$ is vignetted to a high degree by the outlet aperture 36′. The energy throughput characteristic of the instant gas cell is therefore seen to be much superior to that of prior art cells of similar construction.

Figure 3:
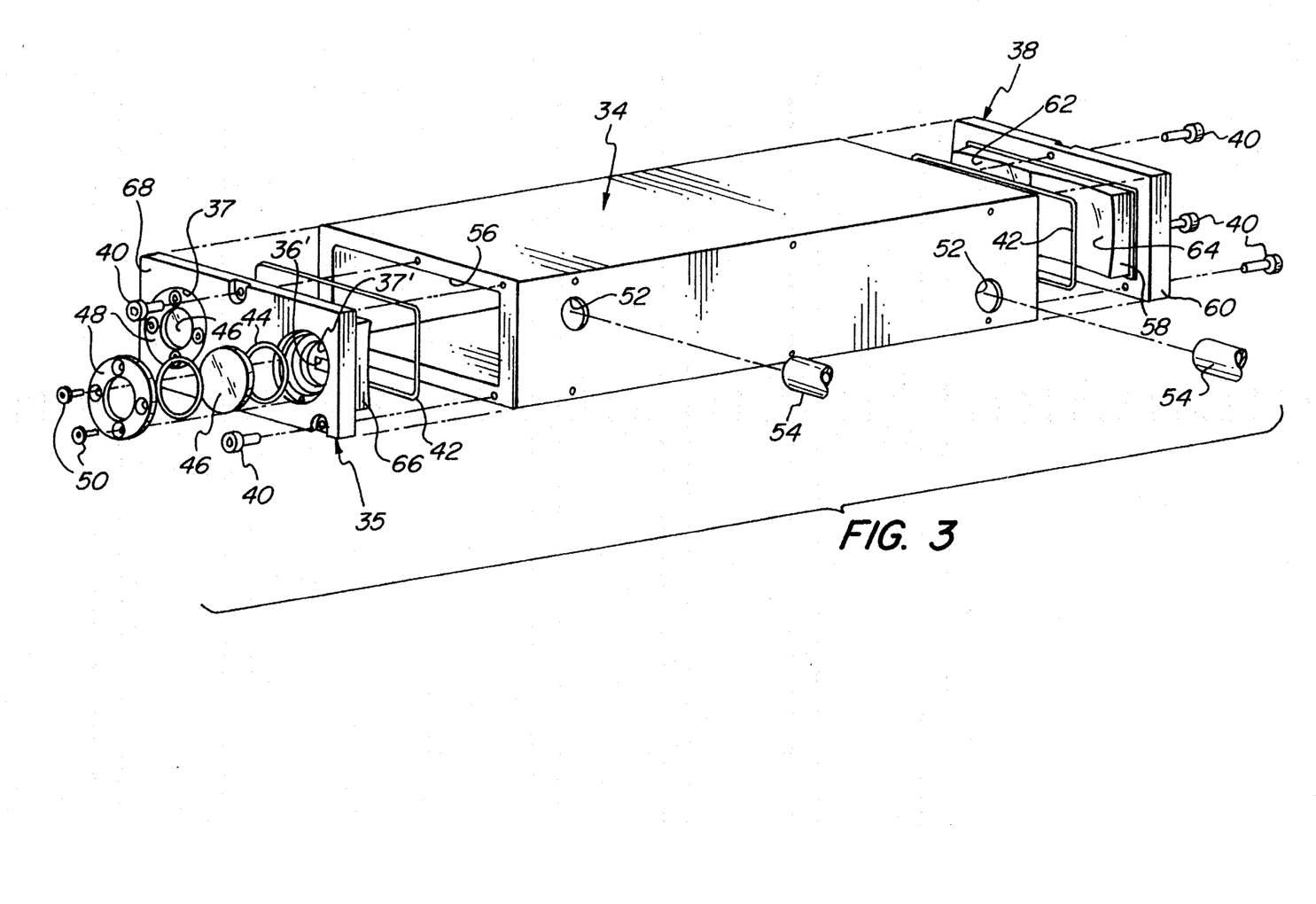
FIG. 3 is an exploded perspective view of a gas cell embodying the present invention.
Figure 4:
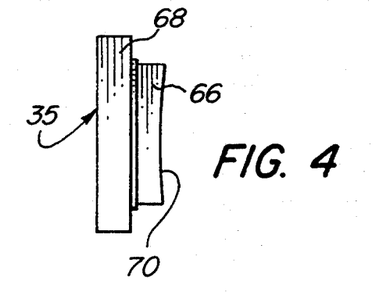
FIG. 4 is an elevational view of one of the end pieces of which the gas cell is comprised.
Figure 5:
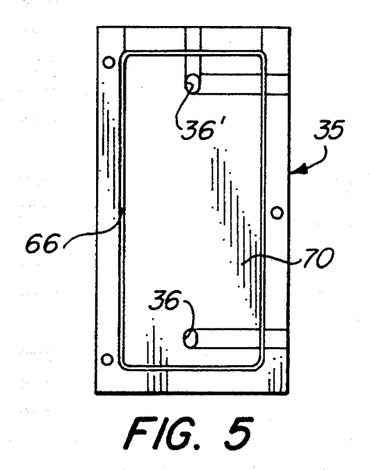
FIG. 5 is a plan view showing the inside surfaces of the end piece of FIG. 4.
Figure 6:
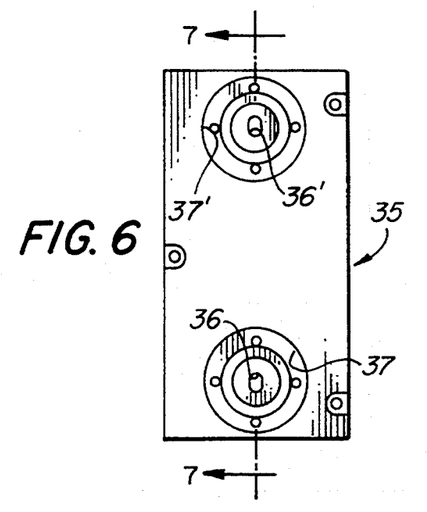
FIG. 6 is a plan view showing the outside surfaces of the same end piece.
Figure 7:
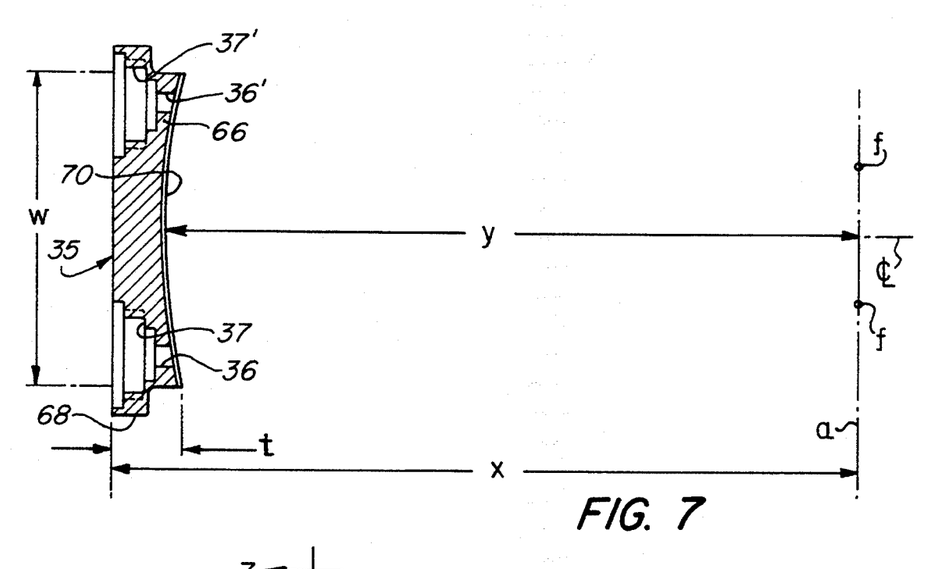
FIG. 7 is a sectional view of the end piece, taken along line 7—7 of FIG. 6.

Turning now to FIG. 3, therein illustrated is the gas cell of the invention, in exploded form. All components are fabricated in relatively thick sections, and from the same grade of high thermal conductivity aluminum. This construction minimizes thermal distortion of the enclosure by causing dimensional changes to occur uniformly throughout, and thereby allows operation of the cell over wide temperature ranges without need for optical realignment.

The end piece 35 is formed with two laterally aligned compound sockets 37, 37′, each of which opens at its inner end through an aperture 36, 36′ (only aperture 36′ being visible in this Figure), respectively, A window 46 of suitable material (e.g., calcium fluoride, potassium bromide and zinc selenide, depending upon the anticipated conditions of operation, radiation wavelength, etc.) is seated in each socket 37, 37′, sealed on its opposite faces by o-rings 44 and held in place by retaining rings 48, using screws 50.

The body 34 of the cell has a passageway 56 of rectangular cross section extending entirely through it and defining the cell chamber, into which block portions 58 and 66 of the opposite end pieces 38 and 35, respectively, are inserted. The end pieces are held in place by screws 40 passing through their respective flange portions 60 and 68, with mating surfaces being sealed by interposed o-rings 42. Openings 52 are formed through one wall of the body 34, and receive conduits 54 for the passage of gases to be analyzed into and from the chamber of the cell.

As is more fully described with reference to FIGS. 4 through 7, an elliptical reflective surface 70 is formed on the body portion 66 of end piece 35. The surface 70 may be regarded as generated about a machining spin axis "a", spaced a distance "x" from the outer surface of the piece, and is formed to have focii at points "f"; the distance "y" on the center-line indicates the closest approach of the reflective surface 70 to the opposite outer surface of the piece. By way of specific example, the distance "x" may have a value 11.6579 inches, "y" may be 10.9449 inches, each focus "f" may be 0.9843 inch from the center-line, the thickness "t" of the piece 35 may be 0.981 inch, and the width "w" may be 4.410 inches.

Figure 8:
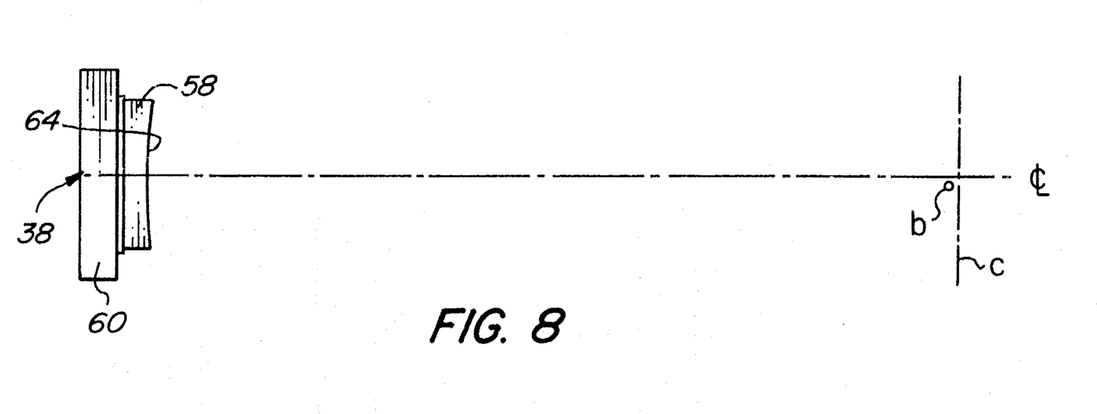
FIG. 8 is an elevational view of the opposite end piece of the gas cell.
Figure 9:
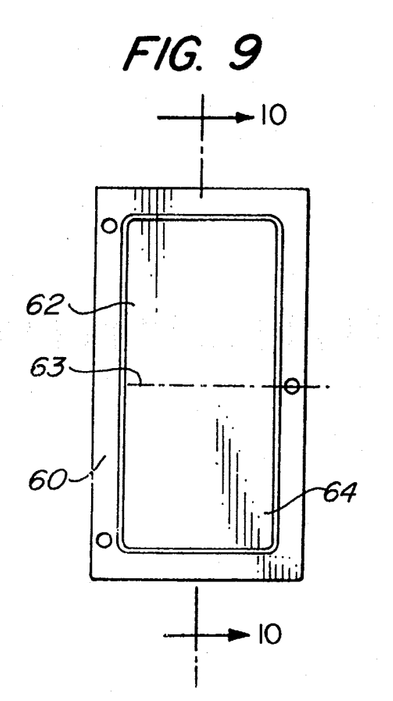
FIG. 9 is a plan view showing the inside surfaces of the end piece of FIG. 8.
Figure 10:
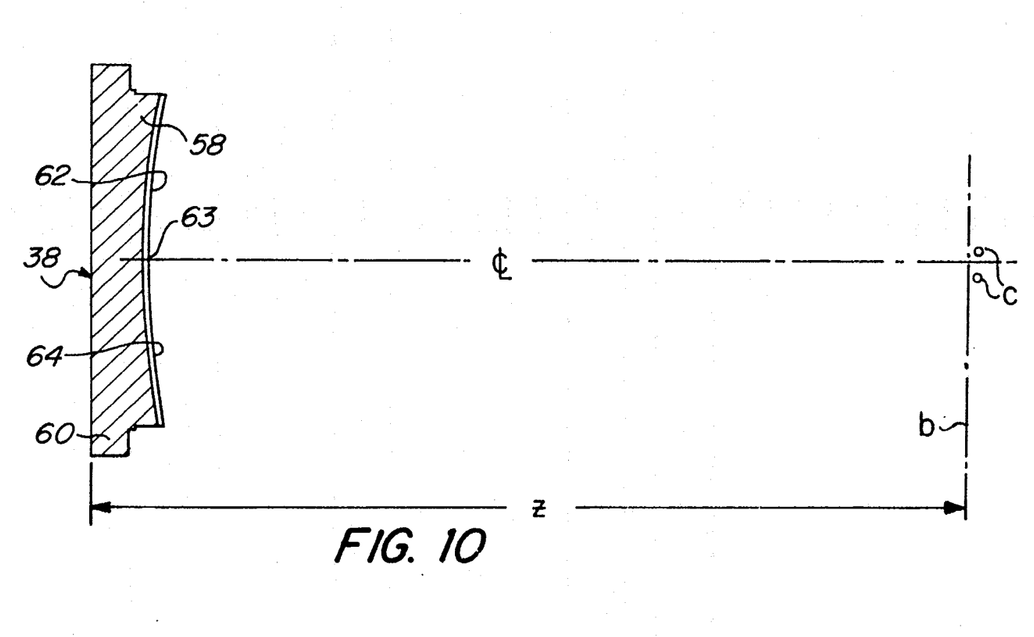
FIG. 10 is a sectional view of the end piece, taken along line 10—10 of FIG. 9.

FIGS. 8 through 10 more fully depict the end piece 38, the body portion 58 of which has produced thereon two side-by-side, generally spherical reflective surfaces 62, 64, which meet at a line of discontinuity 63. Each of the surfaces 62, 64 has a cylindrical component superimposed thereupon, thus providing different radii of curvature in two orthogonal planes and therefore a contour that approaches toroidal. Line "b" in FIGS. 8 and 10 represents a spin axis spaced a distance "z" with reference to the outside surface of the end piece 38, about which the surfaces 62, 64 may be machined; the axes of revolution for the toroids of the surfaces 62, 64 are designated "c". In the exemplary cell, partially described above, the distance "z" may be 11.6406 inches, the axes "c" may be spaced 0.10766 inch behind axis "b" and separated from one another by 0.34670 inch, and surface radii in the plane depicted in FIG. 8 may be 10.9276 inches in length. The thickness and width of end piece 38 may be the same as for piece 35, and in assembly the outer surfaces of the two pieces 35, 38 may be spaced 12.411 inches from one another.

Although the axis of cylinder extends parallel to the axis "b" in the illustrated embodiment, it will be appreciated that it could be perpendicular thereto (albeit with some sacrifice of design and manufacturing facility). Also, cylindrical curvature may be introduced into only one of the surfaces 62, 64 if so desired, and it is believed that negative as well as positive cylindrical curvature may be added. The focii of both objective reflector surfaces are tilted slightly (e.g., 0.09897 inch, in the exemplary cell described) below the centerline in the orientation depicted, to produce the desired rows of images across the field reflector without overlap, as mentioned hereinabove. Although an elliptical field reflector is preferred, other shapes (including spherical, toroidal, etc.) may be substituted if so desired, albeit with some expectation of loss of performance.

An additional feature of the cell, which is believed to be important to its optimal performance, resides in fixing the centers of curvature of the objective surfaces behind the elliptical surface 70. In an assembled unit having the specific construction described above, the centers of curvature of the objective mirrors would optimally lie 0.053 inch behind the elliptical surface; the focii of the elliptical reflector do however lie on the surfaces of the objective mirrors.

It is believed that the objects of the invention are achieved largely through improved coincidence of focus in two orthogonal planes (recognizing that, in even the best case, "focus" is itself essentially a rather amorphous collection of points), thereby controlling distortion, astigmatism, spherical aberration, and coma, and ultimately resulting in maximized energy throughput. Adding the cylindrical component serves of course to reduce the effective radius of curvature in one plane, thus enabling light incident on the reflective surface to better approach the focus in the orthogonal plane.

Although a specific example of a cell embodying the invention has been provided, it will be appreciated that the dimensions and other parameters may vary greatly within the scope of the invention claimed. Particular radii values and other parameters can be determined empirically, by a computer-simulated ray-tracing program, manipulating parameters so as to achieve optimal fidelity between the output and input images.

As noted above, the optical surfaces are most desirably formed directly on the end pieces of which the enclosure is comprised. Although possible by conventional means, such direct formation may be done more economically and effectively by a diamond-machining technique; replication from a diamond-machined master (e.g., by transferring an epoxy-backed gold deposit from the master to the end piece) is also a highly desirable method for producing the reflective surfaces. Fabricated surfaces may of course be rendered fully specular by depositing thereupon a reflective material such as silver, and protective coatings may be applied thereto, as well.

Thus, it can be seen that the present invention provides a folded-path gas cell that is capable of higher radiation throughput and less image blur, as compared to prior art cells of equal or greater size, to thereby afford better operating parameters and to optimize the performance of associated optical instruments by preservation of resolution capability. As compared to a conventional White cell of equivalent dimensions, the optical features of the instant cell render it capable of a 10:1 reduction of blur radius (point spread function), a 4:1 increase in energy throughput, or a 2:1 increase of path length (or any combination thereof). The cell lends itself to construction for minimal distortion and high stability under varying thermal conditions; it is of relatively incomplex design and of relatively facile and economic manufacture. The invention also provides an improved optical instrument incorporating a folded-path gas analysis cell, such as may be especially suited for continuous monitoring of emissions using FT-IR methodology.

Having thus described the invention, what is claimed is:

1. A folded-path radiation absorption gas cell comprising: an enclosure having first and second ends, and defining a substantially closed chamber therewithin; spaced input radiation and output radiation windows formed through said first end of said enclosure and aligned on a first axis; a concave reflective field surface extending at least partially between said windows at said first end of said enclosure; a pair of substantially spherical, concave reflective objective surfaces at said second end of said enclosure disposed in confronting relationship to said field surface, said objective surfaces being aligned side-by-side on an axis parallel to said first axis and in optical registry with said windows, at least one of said objective surfaces having a cylindrical component added thereto to increase coincidence of focii in two orthogonal planes, thereby to maximize the energy throughput characteristic of said cell; and means for the introduction and withdrawal of gas into and from said chamber of said enclosure.

2. The gas cell of claim 1 wherein said cylindrical component extends parallel to said first and second axes, and wherein centers of curvature of said objective surfaces are located behind said field surface.

3. The gas cell of claim 2 wherein both of said objective surfaces are formed with said added cylindrical component.

4. The gas cell of claim 1 wherein said reflective field surface is elliptical, the major axis of said elliptical surface being parallel to said first and second axes.

5. The gas cell of claim 1 wherein at least said ends of said cell are provided by metal components, and wherein said reflective surfaces comprise machined surfaces of said components.

6. The gas cell of claim 5 wherein said enclosure is fabricated substantially entirely of a single metal composition having high thermal conductivity, and wherein the walls of said enclosure are relatively thick so as to afford to said cell optimal thermal-response characteristics.

7. A folded-path radiation absorption gas cell comprising: an enclosure having first and second ends, and defining a substantially closed chamber therewithin; spaced input radiation and output radiation windows formed through said first end of said enclosure and aligned on a first axis; an elliptical concave reflective field surface extending at least partially between said windows at said first end of said enclosure; a pair of substantially spherical, concave reflective objective surfaces at said second end of said enclosure disposed in confronting relationship to said field surface, said objective surfaces being aligned side-by-side on an axis parallel to said first axis, in optical registry with said windows and with their centers of curvature located behind said field surface, at least one of said objective surfaces having a cylindrical component added thereto to increase coincidence of focii in two orthogonal planes, thereby maximizing the energy throughput characteristic of said cell; and means for the introduction and withdrawal of gas into and from said chamber of said enclosure.

8. The gas cell of claim 7 wherein both of said objective surfaces are formed with said added cylindrical component, said component extending parallel to said first and second axes.

9. An analytical optical instrument comprising, in combination:
    (a) a folded-path radiation absorption gas cell comprising: an enclosure having first and second ends, and defining a substantially closed chamber therewithin; spaced input radiation and output radiation windows formed through said first end of said enclosure and aligned on a first axis; a concave reflective field surface extending at least partially between said windows at said first end of said enclosure; a pair of substantially spherical, concave reflective objective surfaces at said second end of said enclosure disposed in confronting relationship to said field surface, said objective surfaces being aligned side-by-side on an axis parallel to said first axis and in optical registry with said windows, at least one of said objective surfaces having a cylindrical component added thereto to increase coincidence of focii in two orthogonal planes, thereby to maximize the energy throughput characteristic of said cell; and means for the introduction and withdrawal of gas into and from said chamber of said enclosure;
    (b) a spectrometer including radiation source means, radiation-discriminating means, and a detector responsive to radiation from said source means; and
    (c) transfer optics, said transfer optics being constructed and arranged to cause a radiation beam from said discriminating means to pass through said gas cell before impinging upon said detector.

10. The instrument of claim 9 wherein both of said objective surfaces of said gas cell are formed with said added cylindrical component, said component extending parallel to said first and second axes; wherein centers of curvature of said objective surfaces are located behind said field surface; and wherein said reflective field surface is elliptical, the major axis of said elliptical surface being parallel to said axes.

11. The instrument of claim 9 wherein said radiation-discriminating means is an interferometer.

* * * * *

(12) EX PARTE REEXAMINATION CERTIFICATE (6859th)
United States Patent
Carangelo et al.

(10) Number: US 5,440,143 C1
(45) Certificate Issued: Jun. 9, 2009

(54) FOLDED-PATH OPTICAL ANALYSIS GAS CELL (75) Inventors: Robert M. Carangelo, Glastonbury, CT (US); David D. Wright, Vershire, VT (US)

(73) Assignee: MKS Instruments, Inc., Andover, MA (US)

Reexamination Request:
No. 90/008,094, Jul. 13, 2006

Reexamination Certificate for:
Patent No.: 5,440,143
Issued: Aug. 8, 1995
Appl. No.: 08/201,814
Filed: Feb. 25, 1994

(51) Int. Cl.
*G01N 21/03* (2006.01)

(52) U.S. Cl. ........................... 250/573; 356/246
(58) Field of Classification Search .................. None
See application file for complete search history.

(56) References Cited

U.S. PATENT DOCUMENTS

| 2,212,211 A | | 8/1940 | Pfund |
| 3,654,801 A | * | 4/1972 | Keefer et al. ............... 73/28.04 |
| 3,989,938 A | * | 11/1976 | Auth ........................... 702/24 |
| 4,749,276 A | | 6/1988 | Bragg et al. |
| 5,009,493 A | | 4/1991 | Koch et al. |
| 5,146,294 A | * | 9/1992 | Grisar et al. ................ 356/435 |

FOREIGN PATENT DOCUMENTS

| GB | 1 571 944 | | 7/1980 |
| GB | 2 240 639 A | | 8/1991 |
| JP | 56066736 A | * | 6/1981 |

OTHER PUBLICATIONS

D. Vukobratovich, "Chapter 3: Optomechanical System Design," in "The Infrared & Electro-Optical Systems Handbook, vol. 4," pp. 121–194 (M. Dudzik, ed., 1993).
C. Denny,, "Metal Mirror Selection Guide Update," in SPIE vol. 181 Contemporary Optical Systems & Components Specifications, pp. 84–89 (1979).
J. White, "Long Optical Paths of Large Aperture," J. Opt. Soc. Am., No. 32, pp. 285–288 (1942).
R. Briesmeister et al., "Long Path Length Temperature-Controlled Absorption Cell for Spectroscopic Studies of Radioactive Compounds," Appl. Spectr., vol. 30, No. 1 (1984).
D. Herriot et al., "Folded Optical Delay Lines," Applied Optics, vol. 4, No. 8, pp. 883–889 (1965).

* cited by examiner

*Primary Examiner*—Lynne H. Browne (57) ABSTRACT

A folded-path gas cell employs an elliptical concave mirror in confronting relationship to two substantially spherical concave mirrors. At least one of the spherical mirrors, and usually both, are formed with an added cylindrical component to increase orthogonal focii coincidence and thereby to increase the radiation energy throughput characteristic of the cell.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3, 5 and 6 are cancelled.

New claims 12–22 are added and determined to be patentable.

Claims 4 and 7–11 were not reexamined.

*12. A folded-path radiation absorption gas cell comprising:*
  *an enclosure having a body and first and second end pieces each comprising a body portion, and defining a substantially closed chamber therewithin;*
  *spaced input radiation and output radiation windows seated in sockets formed through said first end piece of said enclosure and aligned on a first axis;*
  *a concave reflective field surface formed on the body portion of said first end piece of said enclosure and extending at least partially between said windows formed through said first end piece of said enclosure;*
  *a pair of substantially spherical, concave reflective objective surfaces formed on the body portion of said second end piece of said enclosure disposed in confronting relationship to said field surface, said objective surfaces being aligned side-by-side on an axis parallel to said first axis and in optical registry with said windows, at least one of said objective surfaces having a cylindrical component added thereto to increase coincidence of focii in two orthogonal planes, thereby to maximize the energy throughput characteristic of said cell wherein the focii of the objective surfaces are tilted below a centerline of the objective surfaces; and*
  *means for the introduction and withdrawal of gas into and from said chamber of said enclosure.*

*13. The gas cell of claim 12 wherein each window is sealed on its opposite faces by o-rings.*

*14. The gas cell of claim 12 wherein centers of curvature of the objective surfaces lie behind the objective surfaces.*

*15. The gas cell of claim 12 wherein the focii of the objective surfaces lie on the objective surfaces.*

*16. The gas cell of claim 12 wherein the enclosure and its first and second ends are fabricated from relatively thick sections of high thermal conductivity aluminum to minimize thermal distortion of the enclosure.*

*17. A spectrometer comprising the gas cell of claim 12, comprising a radiation-discriminating means, wherein a radiation beam from the radiation-discriminating means passes through said input radiation window of said gas cell before impinging upon a detector of said spectrometer.*

*18. The spectrometer of claim 17 wherein the spectrometer is an infrared spectrometer.*

*19. The spectrometer of claim 18 wherein the infrared spectrometer is a Fourier-transform infrared spectrometer.*

*20. The spectrometer of claim 19 further comprising two openings formed through a wall of the enclosure for monitoring emissions passed into and from the chamber of said enclosure.*

*21. The spectrometer of claim 19 further comprising two openings formed through a wall of the enclosure for continuous monitoring of emissions passed into and from the chamber of said enclosure.*

*22. The gas cell of claim 12 wherein the enclosure and its first and second ends are fabricated from relatively thick sections of high thermal conductivity aluminum to minimize thermal distortion of the enclosure allowing operation of the cell without need for optical realignment.*

\* \* \* \* \*